United States Patent
Jokinen et al.

(10) Patent No.: US 9,226,893 B2
(45) Date of Patent: Jan. 5, 2016

(54) METHOD FOR STORING SILICA-BASED MATERIAL, PACKAGE PRODUCED WITH THE METHOD AND USE OF PACKAGE FOR PACKAGING OF SILICA-BASED PRODUCTS

(75) Inventors: Mika Jokinen, Turku (FI); Mika Koskinen, Turku (FI); Harry Jalonen, Turku (FI)

(73) Assignee: DelSiTech Oy, Turku (FI)

( * ) Notice: Subject to any disclaimer, the term of this patent is extended or adjusted under 35 U.S.C. 154(b) by 1878 days.

(21) Appl. No.: 12/301,195

(22) PCT Filed: May 23, 2007

(86) PCT No.: PCT/FI2007/000136
§ 371 (c)(1),
(2), (4) Date: Nov. 17, 2008

(87) PCT Pub. No.: WO2007/135224
PCT Pub. Date: Nov. 29, 2007

(65) Prior Publication Data
US 2010/0136657 A1    Jun. 3, 2010

Related U.S. Application Data

(60) Provisional application No. 60/802,506, filed on May 23, 2006.

(30) Foreign Application Priority Data

Jul. 24, 2006 (FI) ..................................... 20060698

(51) Int. Cl.
*A61K 9/00* (2006.01)
*A61K 47/02* (2006.01)

(52) U.S. Cl.
CPC ............... *A61K 9/0024* (2013.01); *A61K 47/02* (2013.01)

(58) Field of Classification Search
None
See application file for complete search history.

(56) References Cited

U.S. PATENT DOCUMENTS

| 3,652,761 | A | * | 3/1972 | Weetall | 35/7.32 |
| 3,673,104 | A | | 6/1972 | Albrecht | 252/313 S |
| 5,176,752 | A | * | 1/1993 | Scheiner | 106/737 |
| 5,830,480 | A | | 11/1998 | Ducheyne et al. | 424/400 |
| 5,874,109 | A | | 2/1999 | Ducheyne et al. | 424/486 |
| 6,303,290 | B1 | * | 10/2001 | Liu et al. | 435/4 |
| 6,632,412 | B2 | | 10/2003 | Peltola et al. | 423/338 |
| 2003/0021820 | A1 | | 1/2003 | Ahola et al. | 424/422 |
| 2004/0131982 | A1 | | 7/2004 | Geuens et al. | 430/600 |
| 2004/0219670 | A1 | * | 11/2004 | Cousins et al. | 435/375 |
| 2007/0196427 | A1 | | 8/2007 | Jokinen et al. | 424/426 |

FOREIGN PATENT DOCUMENTS

WO      WO 00/50349       8/2000

OTHER PUBLICATIONS

Nassif et al. "Viability of Bacteria in Hybrid Aqueous Silica Gels". Journal of Sol-Gel Science and Technology, vol. 26 (2003) 1141-1144.*
Bagi et al. "Preservation of Listeria monocytogenes and other pathogenic foodborne bacteria on silica gel". Letters in Applied Microbiology, vol. 17 (1993) 37-39.*
Nassif et al. "A sol-gel matrix to preserve the viability of encapsulated bacteria". J. Mater. Chem., vol. 13 (2003), 203-208.*
Satoh et al. "Functional DNA-Silica Composite Prepared by Sol-Gel Method". Polymer Journal, vol. 37, No. 2, (Feb. 15, 2005), 94-101.*
Wang et al., "Affinity of Antifluorescein Antibodies Encapsulated Within a Transparent Sol-Gel Glass," 65 *Anal.Chem.* 2671(1993).
Peltola et al., "Influence of Sol and Stage of Spinnability on In Vitro Bioactivity and Dissolution of Sol-Gel-derived $SiO_2$ Fibers," 22 *Biomaterials* 589 (2001).
Livage et al., "Encapsulation of Biomolecules in Silica Gels," 13 *J.Phys.:Condens.Matter.* R673 (2001).
Nassif et al., "Living Bacteria in Silica Gels," 1 *Nature Materials* 42 (2002).
Gill, "Bio-doped Nanocomposite Polymers: Sol-Gel Bioencapsulates," 13 *Chem. Mater.* 3404 (2001).
Gill et al., "Bioencapsulation Within Synthetic Polymers (Part1): Sol-gel Encapsulated Biologicals," 18 *TIBTECH* 282 (2000).
Zusman et al., "Purification of Sheep Immunoglobin G Using Protein A Trapped in Sol-Gel Glass," 201 *Anal.Biochem.* 103 (1992).

(Continued)

*Primary Examiner* — Amy L Clark
(74) *Attorney, Agent, or Firm* — James C. Lydon (57) ABSTRACT

A method for storing a water-soluble undissolved silica-based material, optionally with an incorporated functional agent. The method includes immersing the material in an aqueous liquid phase which is initially saturated with a water-soluble silica-based material which is the same or different than the undissolved silica-based material, such that the undissolved silica-based material does not essentially dissolve into the liquid phase during storage, or the proportion of the amount of the initially undissolved silica-based material to the amount of the liquid phase is such that the liquid phase will be saturated or essentially saturated by a dissolved portion of the water-soluble undissolved silica-based material during storage, which dissolved portion of said water soluble undissolved silica-based material is less than 20%. Also disclosed is a storage package which may preferably be used to store functional agents, delivery devices or implants.

15 Claims, 4 Drawing Sheets

(56) References Cited

OTHER PUBLICATIONS

Ferrer et al., "Biocompatible Sol-Gel Route for Encapsulation of Living Bacteria in Organically Modified Silica Matrices," 15 *Chem. Mater.* 3614 (2003).

Kulwinder Flora et al., "Effect of Matrix Aging on the Behavior of Human Serum Albumin Entrapped in a Tetraethyl Orthosilicate-derived Glass," 13 *Chem.Mater.* 4170 (2001).

Avnir et al., "Enzymes and Other Proteins Entrapped in Sol-Gel Materials," 6 *Chem.Mater.* 1605 (1994).

\* cited by examiner

METHOD FOR STORING SILICA-BASED MATERIAL, PACKAGE PRODUCED WITH THE METHOD AND USE OF PACKAGE FOR PACKAGING OF SILICA-BASED PRODUCTS

This application is a National Stage of International Application PCT/FI2007/000136, filed May 23, 2007, which claims benefit under 35 U.S.C. §119 of U.S. provisional application 60/802,506, filed May 23, 2006 and Finnish patent application 20060698, filed Jul. 24, 2006.

FIELD OF THE INVENTION

The present invention relates to a method for storing water-soluble silica-based material with or without a functional agent incorporated in the material. The present invention also relates to a package produced with the method and uses of the package for packaging of silica-based products. More specifically the present invention relates to preserving desired property or properties of silica-based material by storing the material in water-based solution.

BACKGROUND OF THE INVENTION

The publications and other materials used herein to illuminate the background of the invention, and in particular, cases to provide additional details respecting the practice, are incorporated by reference.

Oxygen and silicon are the most and second most abundant elements, respectively, in the earth's crust and consequently a great deal of mass of the Earth's crust is silica (59%). Silica (silicon dioxide, $SiO_2$) is a versatile material that is utilised in great number of applications, such as glass preparation, casting moulds, additive in concrete & cement, pesticides, fertilisers, catalysis, chromatography columns, as xerogel dryer material in desiccators, as aerogel in space dust collection, functional filler in paints or sunscreens, water filtration, drug and gene delivery.

Silica can be obtained from naturals sources by mining and desired modification or by synthesizing it from various precursors. Industrial sand and gravel obtained by mining, often called "silica," "silica sand," and "quartz sand," includes sands and gravels with high silicon dioxide ($SiO_2$) content. Silica can also be prepared/modified to many different structures by fuming or wet synthesis methods, which results in different properties both with respect to textural features and (surface) chemistry.

One of the most interesting features of silica is its interaction with many living organisms and biomolecules. Certain crystal forms of silica are harmful, as in the case of silicosis ("Coal worker's disease"), where inhaled crystalline silica accelerates fibrous tissue overgrowth in lungs, but in amorphous and water-dissolved form silica has been observed to have positive interaction with living organisms and biomolecules. There is also a living example in nature showing the potential of silica for natural contact with living organisms, an example on the phenomenon that is sometimes called biosilicification that results in biogenic silica. One of the most abundant living creatures on earth, diatoms, use the corresponding wet synthesis method to prepare a silica "skeleton" to cover its organic part, i.e., diatoms induce the synthesis of amorphous silica by extracting the needed soluble silica, silicic acid, from sea water that nucleates and condensates on diatoms creating a silica surface.

One of the most studied methods to prepare silica is the sol-gel method. It is done in liquid phase, which makes it potential for many applications. Sol-gel derived $SiO_2$ and other $SiO_2$-based materials are commonly prepared from alkoxides, alkylalkoxides, aminoalkoxides or inorganic silicates that via hydrolysis form a sol that contains either partly hydrolysed silica species and/or fully hydrolysed silicic acid. Consequent condensation reactions of SiOH containing species lead to formation of larger silica species with increasing amount of siloxane bonds. Furthermore, the species aggregate, form nanosized particles and/or larger aggregates until a gel is formed. Reactions (typically at ≤40° C.) are commonly catalysed either by mineral acids (such as HCl and $HNO_3$) or bases (such as $NH_3$). The formed gel is then aged (typically at ≤40° C.), dried to different water content (typically at ≤40° C.) and/or heat-treated (typically at ≤700° C.) to desired form resulting typically in amorphous and porous $SiO_2$. The last step, heat treatment at elevated temperatures (50-700° C.) is typically skipped if the system contains a biologically active agent. The gels that are dried at moderate temperature (at ≤50° C.) are called xerogels (<Gr. xero=dry). The silica gels containing substantial amounts of water, e.g. 30-90%, are sometimes called hydrogels. Amorphous and porous sol-gel derived $SiO_2$ is known to be biocompatible and known to dissolve in the living tissue as well as in solutions simulating the inorganic part of real human body fluid, e.g. in a water solution buffered to pH 7.4 at 37° C. with or without inorganic salts found in real body fluids.

Amorphous silica made by the sol-gel method is known to result in nanoscale porous structure with varying amount of hydroxyl groups on surface. It resembles silica structures formed in biosilicification processes. Such silica has been observed to have specific interaction with living organisms and many biomolecules. It is known to be biocompatible, (e.g., acceptable response observed in tissue) and adjustably biodegradable in simulated physiological conditions and in living tissue. Consequently, sol-gel derived silica and other amorphous silica-based materials are also used as such in biomaterials applications and tissue engineering. Due to possibility for easy encapsulation of different molecules and other active agents by adding them into the reacting sol in liquid phase, silica has also been used as drug delivery device for traditional small-molecule drugs and different biologically and therapeutically active agents, such as proteins and viral vectors.

Encapsulation can also be utilized in many other applications. Many proteins and enzymes are useful in (bio)catalysis or in diagnostic applications as sensors (e.g., antibody-antigen) and they can be encapsulated in sol-gel derived silica, which acts as a carrier material. Also living cells can be encapsulated in silica, where they may act as bioreactors, e.g., by producing therapeutic proteins. Hence, studies on preservation of the biological activity of proteins and other active agents in silica have been one of the topics of interest in different fields of science. In addition to sensitive agents in different biotechnology-related applications, it is also possible to encapsulate other active molecules, which are usually easier cases with respect to preservation of their activity and functionality, such as antimicrobial agents, fragrances, perfumes, colours & dyes, food colours, food additives, antioxidants, humidifiers, vitamins, explosives, insecticides, herbicides, fungicides and high-price reagents/precursors for chemical reactions.

Molecules and other active agents encapsulated in sol-gel silica are in direct contact with different silica species from the liquid phase sol to solid-phase dominating gel, where the condensation and pore structure are under continuous development. Quite substantial shrinkage may occur during the aging and drying processes and also chemical reactions, such as condensation, proceed, so the structure, aging and drying during the storage, may have crucial effects on the activity of the encapsulated agents.

Storage in water-based solution provides a natural and favourable water surrounding to biomolecules, living cells, viruses and other active agents. Drying of sol gel derived silica gel causes shrinkage of the nanoscale pore structure and also results in the formation of a brittle surface structure. Silica is used in many form, such as monoliths, fibres, particles of different size and coatings. The potential applications of fibres are usually composed of structures where silica-silica interaction is present on a macroscopic scale, e.g., in fibre nets or other corresponding structures. In such cases, drying of the silica structure makes the structure loose its flexibility, which is an important property, e.g. in surgical use, e.g., implantation. Some silica formulations may also crack when dried and then replaced in water, e.g. after implantation into living tissue containing a substantial amount of water. This is because the shrinkage of the pore structure during drying is an irreversible process and replacement in water is followed by immediate diffusion of water into the nanoscale pores causing high stresses through capillary forces.

The loss of the activity or viability of proteins, enzymes, viruses, bacteria and other cells in the sol-gel derived silica has been discussed in many publications. The sensitivity to surrounding conditions varies depending on specific agents and there might be differences within species also, e.g., between different proteins. Aging, drying, surface structure, the role of water and alcohol amount in the structure are examples on the factors that may have an influence. One of the major concerns is the long-term stability of biological activity and/or viability of the encapsulated agents as well as the possible breakage of the materials.

Wang et al. [R. Wang, U. Narang, P. N. Prasad and V. Bright, Affinity of antifluorescein antibodies encapsulated within a transparent sol-gel glass, Anal. Chem., 65 (1993) p. 2671-2675] discloses encapsulation of an antibody in a sol-gel matrix and storage of the matrix encapsulating the antibody in water for up to 5 weeks. The sol-gel matrix was stored in water to retain affinity of the antibody.

Livage et al. (J. Livage, T. Choradin and C. Roux, Encapsulation of biomolecules in silica gels, Journal of Physics: Condensed Matter, 13 (2001) p. R673) discussed that sol-gel derived silica is potential for encapsulation of biomolecules and that the internal water in silica has an influence on protein folding, but they also comment that the long term stability of the encapsulation systems should be addressed fully.

N. Nassif et al. (N. Nassif, O. Bouvet, M. N. Rager, C. Roux, T. Choradin, J. Livage, Living Bacteria in silica gels, Nature Materials, vol 1 (2002) p. 42) showed prolonged viability of bacteria in silica gels, but they comment that the long-term viability of cell in inorganics has never been fully addressed.

I. Gill & A. Ballesteros (I. Gill, Bio-doped Nanocomposite Polymers: Sol-Gel Bioencapsulates, Chemistry of Materials 13 (2001) p. 3404 and I. Gill & A. Ballesteros, Bioencapsulation within Synthetic Polymers, TIBTECH vol. 18 (2000) p. 282)) have also reviewed extensively the encapsulation of biomolecules in different silica gels, both xerogels and hydrogels (gels with 50-80% interstitial water and pore sizes between 4-200 nm). However, they address that the hydrogels are usually more or less dried and the structural collapse and shrinkage and a consequent loss of biological activity and breakage of the silica gel structure are common.

Zusman et al. (Zusman et al., Purification of sheep immunoglobin G using protein A trapped in sol-gel glass, Analytical Biochemistry, 201 (1992) p. 103) have also shown that an intact influenza virus entered a sol-gel derived silica gel with high water content (a hydrogel), where it could react with the previously encapsulated sialic-acid-coated liposome indicating thus also indirectly the preservation of the biological activity of the virus during the stay in the silica gel.

M. L. Ferrer et al (M. L. Ferrer, L. Yuste, F. Rojo, F. del Monte, Biocompatible sol-gel route for encapsulation of living bacteria in organically modified silica matrixes, Chemistry of Materials, 15 (2003) p. 3614) concluded in their studies on encapsulation of living bacteria that in addition to alcohol-free system, the main factor affecting the solubility of the encapsulated bacterial cells in the sol-gel silica materials is the control of the physical constraint of exerted by the silica matrix (syneresis) during the aging, i.e., they suspect that the shrinking structure during the aging and drying may reduce the viability of cells.

K. K. Flora and J. D. Brennan (K. K. Flora and J. D. Brennan, Effect of Matrix Aging on the Behavior of Human Serum Albumin Entrapped in a Tetraethyl Orthosilicate-Derived Glass, Chemistry of Materials 13 (2001) p. 4170) have studied albumin encapsulation in TEOS-derived silica gels in different conditions (dry-aged (in air without washing), wash-aged (drying in air after washing) and wet-aged (in buffer) and they concluded that regardless of the method, after 2 months of aging, the entrapped proteins retained less than 15% of their ligand binding ability in solution due to partial unfolding. However, they studied the situation inside the gel only and for albumin only and they did not take into account that the (partial) unfolding, often caused by adsorption to silica pore wall surface or by extensive aggregation of proteins, has been observed to be reversible for many proteins, e.g., it varies depending on the case and this reversible process is also possible as the proteins are desorbed as they are released. Although the structure is shrinking during the aging (independently whether the drying is allowed or not), the simultaneous aging and drying is more effective and the structure may also reach the point where the encapsulated agents do not only adsorb differently, but they may also be physically squeezed in the pores and this occurs naturally faster for larger agents, like cells and viruses. In other words, although the loss of bioactivity is observed inside silica, it may be reversible, but upon too extensive drying, it may become irreversible.

T. Wilson et al. (T. Wilson, R. Viitala, H. Jalonen, R. Penttinen, and M. Jokinen, The Release and Biological Activity of Lysozyme from Selected Sol-gel Derived $SiO_2$ Matrices, submitted to Journal of Materials Science: Materials in Medicine, January 2007) observed that a sol-gel derived silica gel, which had not dried, preserved the activity of released lysozyme, i.e., the amount of biologically active lysozyme corresponded almost 100% to the total amount of released lysozyme with or without separate protective agent, but the activity of released lysozyme was substantially reduced already within few weeks as the gel was let to dry and age simultaneously, i.e., the loss of bioactivity had become irreversible.

D. Avnir et al. (D. Avnir et al., Enzymes and other Proteins Entrapped in Sol-Gel Materials, Chemistry of Materials 6 (1994) p. 1605) reviewed extensively the encapsulation of enzymes, whole cells, antibodies and other proteins in sol-gel materials. They mention wet gels and xerogels, but they do not mention the storage of silica in aqueous solutions, but rather the problems, such as brittleness of the structure of the dried, glassy silica matrix. They are also mostly interested in biological activity in situ in silica gel, where already a reversible loss of biological activity is to be avoided.

M. Jokinen et al. (WO 2005/082781) stored silica implants with encapsulated drugs and other biologically active agents in buffers saturated with silica's dissolution products in order to compare the differences in release mechanisms with an in sink dissolution system, where the silica was let to dissolve freely. The preservation of biological activity or other functional properties of silica or the encapsulated agents were not studied.

P. Ducheyne et al. (U.S. Pat. No. 5,874,109) immersed silica-based implants in aqueous buffer solutions to study the release of encapsulated drugs. This represents a typical and commonly used example in studying silica-based biomaterials where materials are immersed in different buffer solutions mimicking, at least partly, the contents & properties of body fluids to simulate their properties, e.g., ability to precipitate bone mineral-like calcium phosphate (hydroxyapatite), biodegradation property or release of encapsulated agents in vitro.

OBJECTS AND SUMMARY OF THE INVENTION

An object of the present invention is to provide a method for storing a water-soluble undissolved silica-based material, optionally with a functional agent incorporated therein, to preserve desired property or properties of said undissolved silica-based material and/or the functional agent incorporated therein.

Another object of the present invention is to provide a package with a water-soluble undissolved silica-based material, optionally with a functional agent incorporated therein, intended for preserving desired property or properties of said undissolved silica-based material and/or the functional agent incorporated therein.

A further object of the present invention is to provide different uses of the package.

Thus the present invention provides a method for storing a water-soluble undissolved silica-based material of which at least 50%, preferably at least 70% and more preferably at least 90%, calculated as $SiO_2$ of dry matter, consists of $SiO_2$ and/or hydrolysed $SiO_2$, optionally with a functional agent incorporated therein, to preserve desired property or properties of said undissolved silica-based material and optionally of the functional agent incorporated therein wherein said undissolved silica-based material is stored by immersing said material in a liquid phase media comprising water wherein
a) said liquid phase is initially, i.e. when storing is commenced, saturated with a water-soluble silica-based material, which is the same or different than said undissolved silica-based material, to such an extent that said initially undissolved silica based material does not at all or does not essentially dissolve into said liquid phase during storage, or
b) the proportion of the amount of said initially undissolved silica-based material to the amount of said liquid phase is such that said liquid phase will be saturated or essentially saturated by a dissolved portion of said water-soluble undissolved silica-based material during storage, which said dissolved portion of said water soluble undissolved silica-based material is less than 20%, preferably less than 5%, more preferably less than 1%.

The present invention also provides a package with a water-soluble undissolved silica-based material of which at least 50%, preferably at least 70% and more preferably at least 90%, calculated as $SiO_2$ of dry matter, consists of $SiO_2$ and/or hydrolysed $SiO_2$, optionally with a functional agent incorporated therein, intended for preserving desired property or properties of said undissolved silica-based material and optionally of the functional agent incorporated therein wherein said package comprises an essentially closed housing enclosing said undissolved silica-based material immersed within a liquid phase media comprising water wherein
a) said liquid phase is saturated with a water-soluble silica-based material, which is the same or different than said undissolved silica-based material, to such an extent that said undissolved silica based material does not at all or does not essentially dissolve into said liquid phase, or
b) the proportion of the amount of said initially undissolved silica-based material to the amount of said liquid phase is such that said liquid phase will with time in an unopened package be saturated or essentially saturated by a dissolved portion of said water-soluble undissolved silica-based material, which said dissolved portion is less than 20%, preferably less than 5%, more preferably less than 1%.

The present invention additionally provides a use of the package of the invention for preserving a functional agent, preferably a biologically active agent.

The present invention further provides a use of the package of the invention for preserving a device for oral; buccal; rectal; parenteral, including subcutaneous administration, intramuscular administration, intravenous administration and intra-arterial administration; pulmonary, nasal, ocular, intrauterine, vaginal, urethral, topical, and transdermal drug delivery.

The present invention also provides a use of the package of the invention for preserving implants, preferably vascular implants, orthopaedic implants, dental implants or implantable medical devices.

The present invention additionally provides a use of the package of the invention intended for preserving desired property or properties of said undissolved silica-based material wherein said package comprises an essentially closed housing enclosing said undissolved silica-based material immersed within a liquid phase media comprising water wherein
a) said liquid phase is saturated with a water-soluble silica-based material, which is the same or different than said undissolved silica-based material, to such an extent that said undissolved silica based material does not at all or does not essentially dissolve into said liquid phase, or
b) the proportion of the amount of said initially undissolved silica-based material to the amount of said liquid phase is such that said liquid phase will with time in an unopened package be saturated or essentially saturated by a dissolved portion of said water-soluble undissolved silica-based material, which said dissolved portion is less than 20%, preferably less than 5%, more preferably less than 1%
for preserving said water-soluble undissolved silica-based material wherein said use of said water-soluble undissolved silica-based material after having been stored in said package further comprises dissolving said material, preferably in vivo.

DETAILED DESCRIPTION OF THE PREFERRED EMBODIMENTS

Terms

The term silica-based material in the context of this application refers to any material that contains $SiO_2$ and/or hydrolysed $SiO_2$, i.e. SiOH. The material typically contains different amounts of water, remains of precursors and other components used/formed during its preparation process. Typical main products of the matrix are $SiO_2$ and/or hydrolysed $SiO_2$, i.e. SiOH and encapsulated water, which typically represents at least 60% of the materials.

The undissolved silica-based material can comprise any shape and/or form, such as particles, fibres or monoliths and can be e.g. a xerogel or hydrogel. Typically the mean average minimum diameter of the particles or fibres is at least 0.1 μm, preferably at least 1 μm, more preferably at least 10 μm and most preferably at least 0.1 mm.

The term water-soluble when relating to undissolved silica-based material in the context of this application refers to that said material will dissolve in water, albeit sparingly and rather slowly. Typically a water phase saturated by said material comprises 10 to 1000 ppm, preferably 20 to 300 ppm and most preferably 130 to 150 ppm of Si calculated as $SiO_2$. It should be noted, that solubility, i.e. the saturation concentration, is pH dependent. Typically said material would dissolve into water at room temperature at a rate of about 0.02 to 10% (w/w)/h, preferably 0.04 to 2.5% (w/w)/h more preferably 0.08 to 0.6% (w/w)/h and most preferably 0.15 to 0.3% (w/w)/h provided pH<9.

Biologically active agent in the context of this application refers to any organic or inorganic agent that is biologically active, i.e. it induces a statistically significant biological response in a living tissue, organ or organism. The biologically active agent can be a medicine, peptide, protein, polysaccharide or a polynucleotide. It can be a living or dead cell or tissue, bacteria, a virus, a bacteriophage and a plasmid or a part thereof. It can be an agent for treatment of diseases in therapeutic areas like alimentary/metabolic, blood and clotting, cardiovascular, dermatological, genitourinary, hormonal, immunological, infection, cancer, musculoskeletal, neurological, parasitic, ophthalmic, respiratory and sensory. It can further be for treatment of diseases like osteoporosis, epilepsy, Parkinson's disease, pain and cognitive dysfunction. It can be an agent for the treatment of hormonal dysfunction diseases or hormonal treatment e.g. for contraception, hormonal replacement therapy or treatment with steroidal hormones. It can further be an agent such as an antibiotic or antiviral, anti-inflammatory, neuroprotective, prophylactic vaccine, memory enhancer, analgesic (or analgesic combination), immunosuppressant, antidiabetic or an antiviral. It can be an antiasthmatic, anticonvulsant, antidepressant, antidiabetic, or antineoplastic. It can be an antipsychotic, antispasmodic, anticholinergic, sympathomimetic, antiarrhythmic, antihypertensive, or diuretics. It can be an agent for pain relief or sedation. It can also be a tranquilliser or a drug for cognitive dysfunction. The agent can be in a free acid or base form, a salt or a neutral compound. It can be a peptide, e.g. levodopa; a protein, e.g. a growth factor; or an antibody. It can be a polynucleotide, a soluble ion or a salt.

In the context of this application the term implant refers to any device that is meant to be inserted, at least partially, into a mammal, including human.

In the context of this application the term device for drug delivery refers to any thing made or adapted for drug delivery.

Features of the Invention

The general aim of the invention is to store biodegradable silica-based materials in water-based medium to stop the biodegradation that occurs by dissolution in water. Due to low solubility of silica in water, the biodegradation can be stopped conveniently by choosing a proper medium volume or by putting silica-based materials into ready-saturated (with respect to silica's dissolution products) solution. The low solubility is not a problem for a possible desired biodegradation, because the liquids can also be changed. For example, in case of implantation into body, the body fluids flow and are renewed daily, i.e. an implant degrades in the body by dissolution in spite of the low solubility. A further aim is to reduce/stop the evolution of the dynamic silica-based structure, e.g. the strong shrinkage caused by free drying that may destroy desired properties, such as biological activity or mechanical properties, or any other applicable activity/function, by storing it in a water-based storage medium. Silica may be stored in any storage medium consisting of a liquid where water is an essential component. The pH may be chosen freely as long as the solubility is low enough in proportion to water volume for silica-based material not to totally dissolve in the storage liquid. The storage medium is preferably a buffered solution mimicking body fluid conditions at 0-37° C. and buffered to pH 7.0-7.5. If desirable, also temperatures below 0° C. with additives that lower the freezing point of the water solution could be used or alternatively the water could be frozen. When selecting the pH, the specific properties of materials possibly encapsulated have to be taken into account. Many biologically active and therapeutic agents do not tolerate high or low pH, but beyond medical applications, there may be also other options for pH.

Silica or silica-based materials should preferably be totally immersed in the storage liquid so that it in any position of a package remains fully immersed. Saturation may be take place spontaneously through dissolving of the material or the liquid may be separately ready-made to include dissolved silica species at saturation.

The silica-based material does not have to be pure silica, it may contain different amounts of water, remains of precursors or other components. In practice, the silica-based materials contain always some water encapsulated in the structure. The silica-based material to be stored in water-based medium may also contain substantial amounts of water and the solid phase may still be dominating or it may be substantially dried. For example, a silica hydrogel may contain, e.g., 30-90% water and it can be used as an implant as well as a silica xerogel dried to the equilibrium (with respect to the surrounding conditions). The silica-based material may be of any origin, crystalline, amorphous or including both forms, it can be prepared by any method, e.g. by chemical modification of mined quartz sand or by precipitation of silica-containing solution, but it is preferably prepared by the sol-gel method. The precursors may include any common components used to prepare silica-based materials by the sol-gel method, e.g., by organic silicates such as alkoxides, aminoalkoxides, alkylalkoxides or by inorganic silicates, such as sodium or potassium silicates or (poly)silicic acids etc.

The materials are preferably made of sodium or potassium silicates or alkoxides [$Si(OR)_4$; $R=C_xH_y$, preferably $C_2H_5$] that are fully or partly hydrolysed in water to silicon hydroxides [$Si(OH)_y$] and further condensed fully or partly to siloxanes (—Si—O—Si—), i.e., silica. E.g., alkoxides $Si(OR)_{4-y}(OH)_y$, e.g., tetraethylortho-silicate=tetraethoxysilane $Si(OC_2H_5)_{4-y}(OH)_y$.

For example, a silica-based material may contain silica, silicon hydroxide, encapsulated water $(Si_n(OH)_{2x}O_{2n-x}+zH_2O)$, reaction product alcohol and remains of the precursors $Si(OR)_{4-y}(OH)_y$ that has partly or fully hydrolysed and/or condensed. The unreacted or partly reacted $[Si(OR)_{4-y}(OH)_y]$ may also be integrated with $Si_n(OH)_{2x}O_{2n-x}+zH_2O$ in any proportion with respect to chemical bonds with silicon or physically in pores. $[Si(OR)_{4-y}(OH)_y]$ and/or $Si_n(OH)2xO_{2n-x}+zH_2O$, integrated and/or separately, may be included in nanoscale particles that are constituents of the bulk structure of the silica-based materials such as monolithic structures (rods, tablets etc.), larger particles (e.g., microspheres), fibres, coatings etc. and integration between the nanoscale particles may occur by chemical bonds or by any other interaction forces, such as electrostatic or van der waals forces.

The mass of the silica-based material stored and the volume of the water solutions are preferably adjusted so that saturation occurs rather fast and without significant degradation of the materials. The solubility of amorphous, sol-gel derived silica at pH 7.0-7.5 is most commonly about 130-150 ppm (=µg/ml) at temperatures near room temperature. Also totally crystalline silica has low solubility (a few ppm) at same conditions meaning in practice that all forms of silica are biodegradable. Solubility and saturation should in this context be understood so that the dissolution has practically stopped. Amorphous silica and crystalline silica have been reported to have different solubility in water and bigger differences (than within 130-150 ppm) have also been reported between different amorphous silicas. Silica may, e.g., partly stabilise its own structure by reprecipitation and/or remodelling of the surface. Hence, the observed values do not necessary represent thermodynamically defined solubility, but rather a dissolution level after which nothing significant occurs in practice. For example, if the dissolved amount of silica is 40 ppm after one day and dissolution proceeds only 1% within the next year, the level of 40 ppm after one day is practically applicable to be used in the described storage system.

Low solubility of silica at body fluid-like conditions is utilised to prevent possible problem-causing reactions of SiOH— and water-containing silica-based material with packing materials and to prolong the storage time and preservation of biological activity of sensitive biologically active, therapeutic or other functional agents, which have been encapsulated in silica-based materials. The reactive and/or biodegradable, silica-based material, which contains both free hydroxyl groups and encapsulated water, may interact/react with any packing material commonly used and cause degradation or harmful modification of the packing or changes in silica-based material's own properties. By filling the package with water solution that is quickly saturated by silica's degradation products, the direct interaction with packing material can be essentially reduced.

In addition, there are results that show that some biologically active agents, such as proteins and viral vectors, preserve their biological activity when stored in water-containing silica rather than in dried structures. By storing the silica in water solution, the wetness or water as the essential phase of the liquid in the porous structure of silica-based materials can be maintained. Water in the structure is favourable for proteins to preserve its native structure and a natural environment for living agents encapsulated, i.e., viruses, cells and bacteria.

Many preferred embodiments aim at enabling controlled release of the undissolved silica-base material as such (e.g. when acting as a functional agent), and/or the functional agent optionally incorporated within it by dissolution of the material. Dissolution and resulting release typically takes place at the site of action of the functional agent. Accordingly, depending on the application, release can take place e.g. in vivo, in vitro and in the field, e.g. if the functional agent is an herbicide. Controlled release can be achieved by controlled dissolution, i.e. dissolution of the material within a desired time period, of the silica-based material. Dissolution rate and resulting release rate can be adjusted based on techniques know in the art (e.g. WO 01/40556, WO 00/550349 and WO 2005/082781) and the specific conditions at the site of dissolution.

From the viewpoint of the release mechanism, the storage system is suitable for any encapsulated agents that stay in the structure, such as cells or bacteria or are released mainly by silica matrix material degradation, such as peptides, proteins, polysaccharides and viruses, but also some smaller molecules as long as the diffusion from the typical pores of sol-gel derived silica are small enough and the release is mainly covered by the silica-based materials degradation. It is also very likely that the silica-based material as such, especially as it contains any amount of water, is reacting and changing with time, at least some parts of the material may slowly condense further and if it is also drying, it may also affect the surface of the material, e.g., by becoming brittle. Hence, if the storage in water does not affect the functionality of the material, it is also favourable to store it with the introduced method.

The main application area of the invention is for storage of silica-based materials in medical and dental use as biomaterials, as such, or as delivery and/or encapsulation devices for drugs and other therapeutically active agents, such as therapeutic peptides, proteins, polysaccharides, non-viral and viral vectors, cells, bacteria in, e.g., medical device, tissue engineering scaffolds or other implants, prostheses or injectable devices, but it can also be applied to any application where silica is utilized in encapsulation and/or controlled release of different functional agents, e.g., in cosmetics, diagnostics, sensors, reflecting surfaces, fragrances, perfumes, colours & dyes, food colours, food additives, antioxidants, humidifiers, vitamins, explosives, insecticides, herbicides, fungicides, fodder, plant hormones, plant foods, enzymes, antibodies, veterinary drugs, antimicrobial agents, anti-inflammatory agents, catalysts, reagents, UV-absorption, sunscreens.

Preferred Embodiments

In typical embodiments use of the water-soluble undissolved silica-based material after having been stored according to the invention comprises dissolving said material, preferably in vivo, optionally resulting in release of the functional agent incorporated therein.

In typical embodiments the silica-based material saturating or essentially saturating the liquid phase essentially consists of silicic acid, i.e. $Si(OH)_4$. The liquid phase media typically comprises at least 1%, preferably at least 50%, more preferably at least 90% and most preferably at least 98% water. The pH of the liquid phase media is typically <9, preferably from 5.0 to 8.0 and more preferably from 7.0 to 7.5.

In preferred embodiments the undissolved silica-based material is sol-gel derived. The undissolved silica-based material typically comprises at least 0.3%, preferably 1.0%, more preferably 3.0%, even more preferably 10%, and most preferably 30% Si compounds calculated as $SiO_2$.

In many preferred embodiments of the invention the sol-gel derived material is immersed in the liquid phase media only after the material has been aged and/or dried to the extent that the weight of said material is ≤90%, preferably ≤70%, more preferably ≤50% and most preferably ≤40% of the weight of the corresponding sol, i.e. the sol wherefrom the material is derived.

In some typical embodiments the desired property to be preserved is a property of the undissolved silica-based material as such, i.e. excluding an optionally incorporated functional agent, and the property is preferably the biological activity and/or mechanical property or structure of the silica-based material as such.

In many embodiments a functional agent, preferably a biologically active agent, is incorporated in the undissolved silica based material. In some preferred embodiments the functional agent is a biologically active agent; preferably a living micro-organism or spore thereof, or a living animal or plant cell. If the functional agent is a living micro-organism or a spore thereof, it is preferably selected from the group consisting of viruses, bacteria, protozoa and fungi.

In some preferred embodiments the biologically active agent is a nucleic acid, preferably selected from the group consisting of DNA, RNA and plasmids.

In different preferred embodiments of the method the undissolved silica-based material is stored for at least 1 week, 1 month, 3 months, 1 year and even 5 years.

In typical embodiments of the package of the invention the proportion of the amount of the undissolved silica-based material to the amount of the liquid phase is such that less than 20%, preferably less than 5%, more preferably less than 1% of the undissolved silica-based material will with time be dissolved in the liquid phase. In many typical embodiments of the package of the invention the liquid phase comprises more than 20 ppm, preferably more than 100 ppm, more preferably about 130 to 150 ppm of Si calculated as $SiO_2$.

Preferred uses of the invention are for preserving living micro-organisms or spores thereof, or living animal or plant cells. If used for preserving a micro-organisms or spore thereof the micro-organism is preferably selected from the group consisting of viruses, bacteria, protozoa and fungi.

In some preferred uses of the invention nucleic acid, preferably selected from the group consisting of DNA, RNA and plasmids, are preserved.

In especially preferred embodiments of the invention use of the invention further comprises, after storage according to the invention, dissolving the undissolved silica-based material preferably in vivo, resulting in release of the functional agent if incorporated therein. These embodiments can comprise use of the package of the invention comprising the water-soluble silica-based material with or without the functional agent incorporated therein.

EXAMPLES

Example 1

Recombinant adenoviruses (serotype 5) with an *E. coli* LacZ marker gene are encapsulated in silica during the sol-gel process. The biodegradable (dissolvable) silica samples are then soaked into an aqueous solution, in phosphate buffered saline, PBS at +37° C. and pH 7.4 for different times. Due to low water-solubility of silica, the buffer is quickly saturated with respect to the silica's dissolution products and the degradation of silica stops.

At different time points the silica samples have been cultured with human skin fibroblasts and cells have been X-Gal stained. After staining it can be noticed (microscopically) from the desired colour that the marker gene LacZ has been transferred into the cells, which occurs if the cells have been infected by the viruses. This shows that adenoviruses are still biologically active and capable of transferring genes into the cells after 28 days' storage in PBS at +37° C. and pH 7.4 that is saturated with respect to the silica's dissolution products.

After 32 days in PBS at +37° C. and pH 7.4, no activity can be observed. The same virus looses most of its activity in plain PBS at +37° C. and pH 7.4 already after 1 day and totally after 4 days. If the samples are let to dry, no adenovirus activity or gene transfer into the cells is observed.

Figure 1:
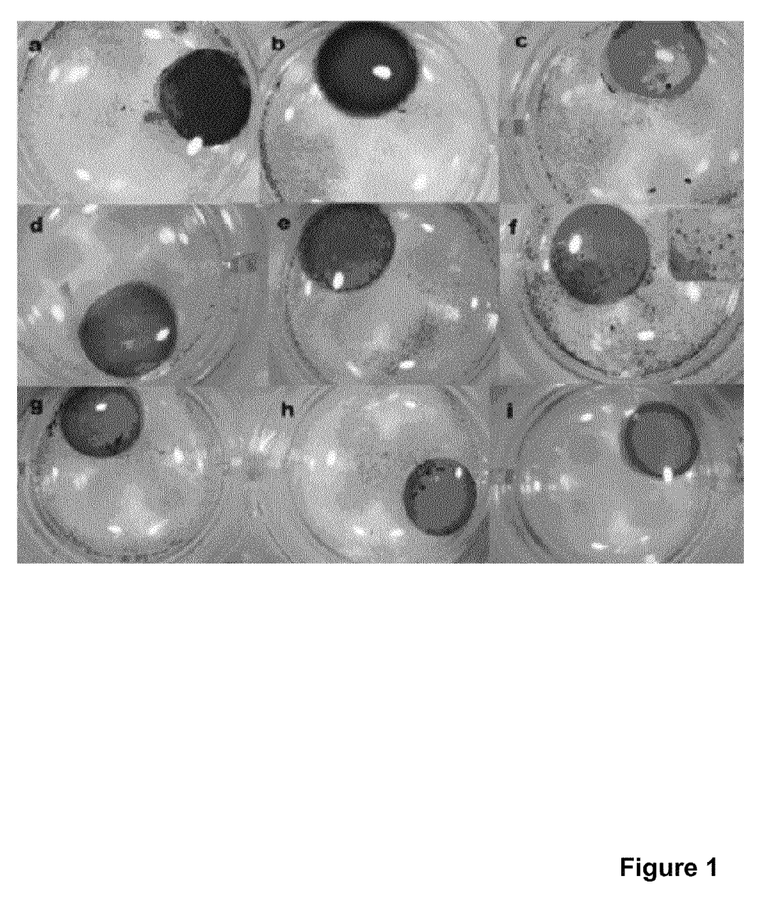
FIG. 1 demonstrates successful gene transfer using an adenovirus stored according to the method of the invention.

FIG. 1 shows a blue colour (dark in black and white pictures) indicating successful gene (LacZ) transfer after X-gal staining of human skin fibroblasts cultured with in an aqueous buffer (PBS at 37° C. and pH 7.4) stored silica implants with encapsulated recombinant adenoviruses (serotype 5) with an *E. coli* LacZ marker gene. The different pictures a, b, c, d, e, f, g, h and i show transfer (or lack of transfer) when stored for 4, 7, 11, 13, 18, 21, 25, 28 and 32 days respectively. Adenoviruses are still active after 28 days of storage in PBS ("h"), but after 32 day ("i") no activity can be observed.

Figure 2:
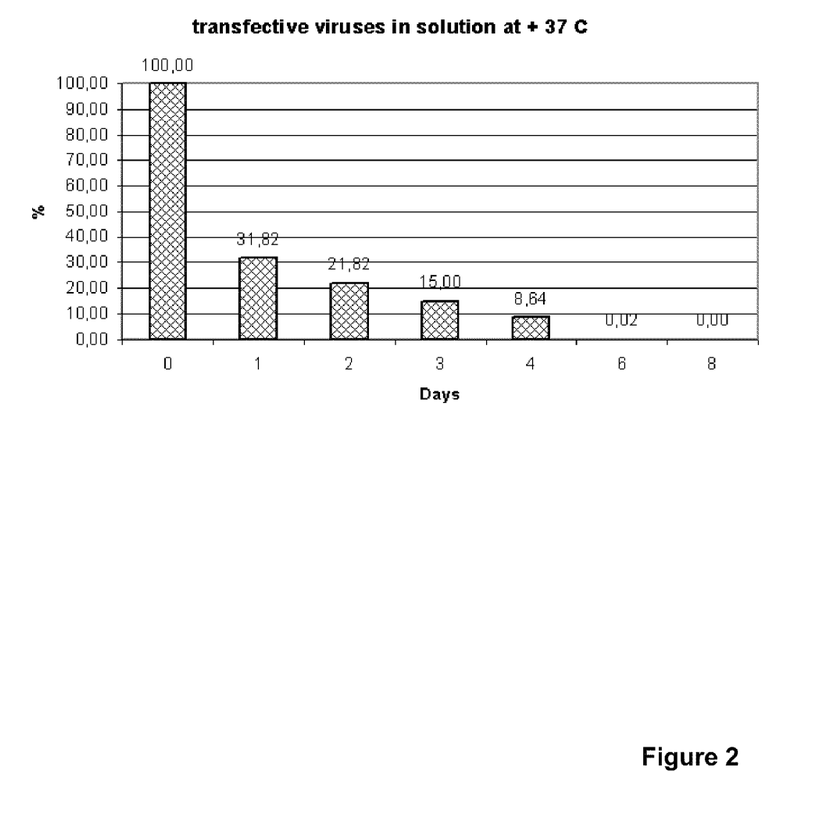
FIG. 2 shows for comparison survival of recombinant adenovirus in plain PBS

FIG. 2 shows for comparison survival of recombinant adenoviruses (serotype 5) with an *E. coli* LacZ marker gene in plain PBS at +37° C. and pH 7.4.

Example 2

Recombinant adenoviruses (serotype 5) with an *E. coli* LacZ marker gene are encapsulated in silica during the sol-gel process. The silica samples are kept in a ready-saturated aqueous solution (with respect to silica's dissolution products) 0.05 M TRIS (Tris-chloride, e.g., Trizma preset Crystals, Sigma) buffer at +2.2° C. (pH 7.0-8.0) for 229 days. Prior to the cell culture, the silica samples are let to dissolve in greater dissolution medium volume (in phosphate buffered saline, PBS at +37° C. and pH 7.4) for 3 days during which 10-30% of silica is dissolved. This is done in order to determine whether the adenoviruses encapsulated deeper in the bulk of silica are also active. After 3 days in PBS the silica samples are transferred to a culture of human skin fibroblasts. After X-Gal staining it can be noticed (microscopically) from the desired colour that the marker gene LacZ has been transferred into the cells, which occurs if the cells have been infected by the viruses. This shows that adenoviruses, also deeper in the bulk of silica, in fact are encapsulated in silica and are still biologically active and capable of transferring genes into the cells after 229 days' storage in TRIS buffer at +2.3° C. that is saturated with respect to the silica's dissolution products. Further storage studies showed some activity up to 571 days of water storage at 2-4° C. Corresponding samples stored at room temperature (20-25° C.) showed some activity after 430 days of water storage.

Figure 3:
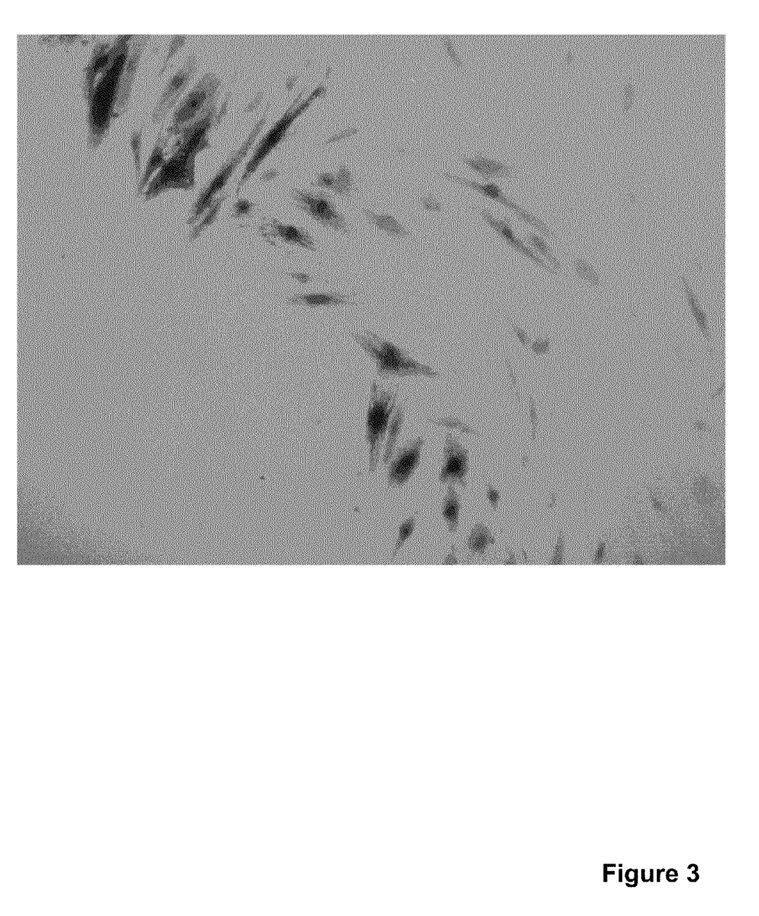
FIG. 3 demonstrates successful gene transfer using adenovirus stored according to the method of the invention.
Figure 4:
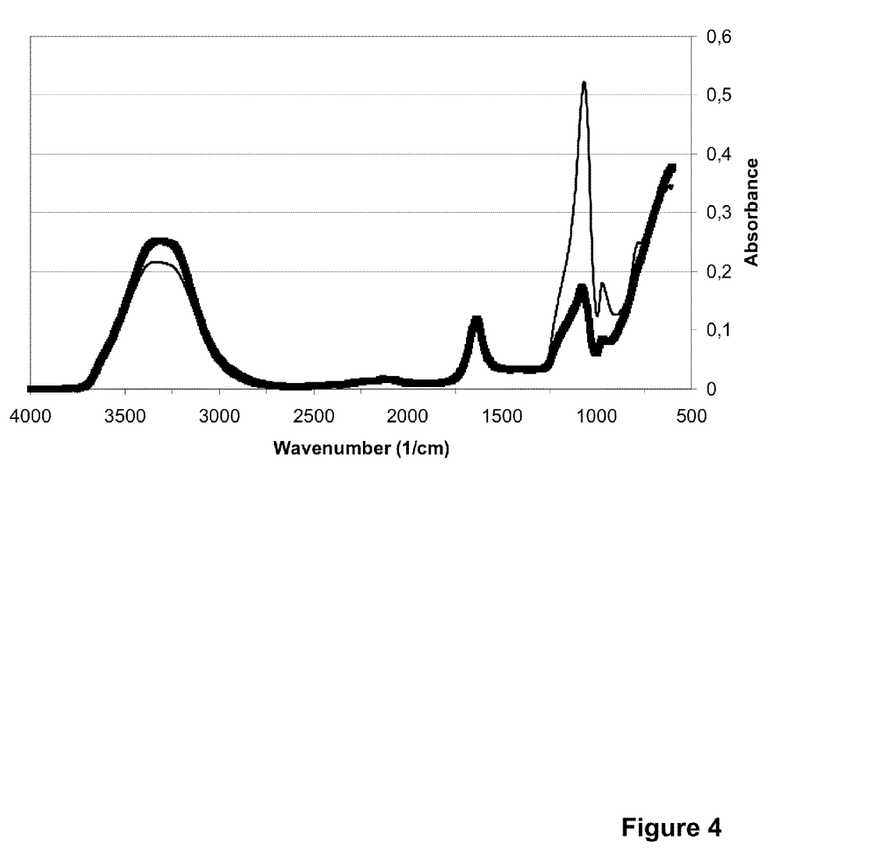
FIG. 4 shows IR spectrums' of a freshly-measured (5 d) silica gel implant and that of an implant after 98 days of storage in water.

FIG. 3 shows a blue colour (dark in a black and white picture) indicating successful gene (LacZ) transfer after X-gal staining of human skin fibroblasts cultured with in an aqueous buffer (Tris-chloride at 2.3° C. and pH 7.0-8.0 for 229 days) stored silica implants with encapsulated recombinant adenoviruses (serotype 5) with an *E. coli* LacZ marker gene.

Example 3

Sol-gel derived silica fibres are made into three dimensional structures by letting the just-made, still partly wet fibres, or separately in aqueous solutions partly dissolved and wet fibres to gather freely on top of each other in layers. The net-like structure of fibres having fibre-fibre contacts retains its flexibility as long as the structure is wet. If the structure is let to dry, the net-like structure becomes brittle loosing its flexibility. By placing the sol-gel derived silica fibre in net-like structures in an aqueous solution that is rather quickly saturated (by matching the volume and the typical solubility of silica at neutral conditions at 130-150 ppm) with respect to the silica's dissolution product, the degradation (dissolution) of silica stops facilitating the preservation of the structure.

Example 4

Monolithic silica structures planned to be used as implants, e.g., rods, are let to dry to constant weight at ambient condition at 0-40° C. These silica structures are still partly wet after reaching constant weight, but in practice they reach equilibrium with the surrounding conditions. Some silica samples, especially those made with rather low water-to-alkoxide (TEOS, tetraethyl orthosilicate) ratios (R) at R<5 and most commonly at R<3 break into pieces as they are replaced in aqueous solutions, e.g., in saline (physiological salt solution), in TRIS (Tris-chloride) buffer kept at +37° C., or in the simulated body fluid (SBF by Kokubo et al.) kept at +37° C. and pH 7.4. Breakage into pieces caused by the capillary forces after water diffusion into small pores of sol-gel derived silica is not observed if the monolithic silica samples are stored in aqueous solutions, e.g., in saline (physiological salt solution), in TRIS or in SBF, which are saturated with respect to the silica's dissolution products.

Example 5

It was observed that the aging of the sol-gel derived silica gel structure prior to water storage is crucial for the stability of the silica gel implants. If sol-gel derived silica gel implants are immersed into water too early after the gel formation, i.e. when the silica structure is very immature and/or the silica gel still contains a lot of liquids from the sol phase, the implants tend to swell and/or break during storage. This was observed by comparing the preparation process of the exactly same silica formulation (sol's water-to-TEOS ratio 52.5; corresponding implants as in Examples 1 and 2, but without the encapsulated viruses) in two batches (in cylindrical moulds with a volume of 400 µl and with a diameter of ca. 1 cm) with different production quantities, i.e. one 20 implants' batch and another 40 implants' batch. The moulds for each batch, were kept open in a Nalgene desiccator (5317-0120; 30×30× 30 cm) at 4° C. for 24 h. The weight of the implants of the 20 implants' batch was ca. 45±5% compared to the weight of the corresponding sol (linear decrease as a function of time from 100% to 45% in 24 hours). These implants did not swell and they became mechanically stronger with water-storage time and they were easy to handle, e.g. they did not break when handled with forceps. The exactly same procedure for a 40 implants' batch in exactly the same conditions yielded silica gel implants that started to swell after ca. 1 month's storage in water. The weight loss of these implants during aging and drying in the desiccator for 24 h was not determined. In addition, these silica gel implants were clearly softer than those made in the 20 implants' batch. The swollen silica gel implants broke easily into pieces, e.g. when the storage liquid was stirred or when the implants were removed from the storage vessel by pouring them with liquid onto a plate for further use. This shows that insufficient aging and/or drying of the sol-gel derived silica gel implants prior to water storage nor too severe drying of implants (silica gel implants dried into the constant weight as described in Example 4), are typically not to be preferred.

Example 6

FT-IR measurements (FIG. 4) performed using Perkin Elmer Spectrum BX FT-IR System with the ATR mode show that the chemical structure of silica gel implant samples (sol's water-to-TEOS ratio 52.5; corresponding implants as in Examples 1 and 2, but without the encapsulated viruses) do not significantly change during 98 days of storage in water, but the water content in the silica gel implants does.

In FIG. 4 the thicker line shows the IR spectrum of the freshly-measured silica gel implant (5 days in water-storage) and the thinner line the IR spectrum of the corresponding silica gel implant stored for 98 days. Overlapping of the spectra is quite extensive and the same peaks are found in both spectra, only their relative ratios have changed. Peaks at around 3300 $cm^{-1}$, 1060 $cm^{-1}$ and 970 $cm^{-1}$ indicate changes in water content and increased amount of condensed Si—O—Si during the 98 day's storage in water. The ratio between the peaks at 1060 $cm^{-1}$ and 970 $cm^{-1}$ for the fresh silica gel samples and silica gel samples stored in water for 98 days were 2.3 and 2.8, respectively.

The ratio between the peak at 3300 $cm^{-1}$ and 1060 $cm^{-1}$ was used for analysing the water content. The ratio between the peaks for the freshly-measured silica gel implant (5 days), when water-stored for 41 days and when water-stored for 98 days was 1.16, 0.84 and 0.36, respectively. The water content (w/w) determined by thermogravimetric analysis (Perkin-Elmer TGA7) was 89.2% for the silica gel sample stored for 41 days. Corresponding water content 88%±5% has also been observed for the same silica gel formulation after shorter storage times. The relation between the FT-IR peak ratio and the storage time gave a linear relationship as did that of the silica content (w/w) and FT-IR peak ratio. By using the linear relationship for the FT-IR peaks ratio and the weight loss for the silica gel implant stored for 98 days, the water content (w/w) was determined to be 43.5% meaning that clear decrease in the water content inside the silica gel implants occurred between 41 and 98 days, but no significant changes were observed before 41 days of storage in water.

Biodegradation rate of the corresponding silica gel implants were measured in a TRIS buffer solution (pH 7.4, 37° C.) in a shaking water bath. Silica dissolution was measured with a spectrophotometer (UV-1601, Shimadzu) analyzing the molybdenum blue complex absorbance at 820 nm. The results show that the fresh silica gel implants dissolve on average 2.0% (w/w)/h, but the dissolution rate decreases already after 25 days' water storage to ca. 1.1% (w/w)/h and no significant change is observed after 4 months' storage, when the dissolution rate is still ca. 1.1% (w/w)/h. This shows that aging (condensation) of the silica structure proceeds faster than the decrease in the water content of the implants.

The invention claimed is:

1. A method for storage of an implant or delivery device, comprising the steps of:

i.) providing an implant or delivery device, said implant or delivery device comprising a water-soluble, undissolved silica-based material consisting of $SiO_2$ and/or hydrolysed $SiO_2$, said water-soluble, undissolved silica-based material comprising at least 50% of dry matter calculated as silicon dioxide ($SiO_2$), said water-soluble undissolved silica-based material further comprising a functional agent incorporated therein;

ii.) immersing said implant or delivery device in a liquid phase comprising water, such that a) said liquid phase is saturated with a water-soluble silica-based material, which is the same or different than said water-soluble, undissolved silica-based material, wherein said water-soluble, undissolved silica-based material does not at all or does not essentially dissolve into said liquid phase during storage, or b) an amount of said water-soluble, undissolved silica-based material is dissolved into said liquid phase, thereby saturating the liquid phase, with the proviso that the dissolved amount of said water-soluble silica-based material is less than 20% of an initial amount of said water-soluble, undissolved silica-based material; and iii.) storing said implant or delivery device in said liquid phase for at least three months, wherein said functional agent is a biologically active agent selected from the group consisting of viruses, a living micro-organism or a spore thereof, living animal cells, living plant cells and a nucleic acid.

2. The storage method of claim 1, further comprising the step of:

dissolving said water-soluble, undissolved silica-based material resulting in release of said functional agent.

3. The storage method of claim 1, wherein the liquid phase is saturated or essentially saturated with $Si(OH)_4$.

4. The storage method of claim 1, wherein the liquid phase comprises at least 1% water.

5. The storage method of claim 1, wherein the pH of the liquid phase is <9.

6. The method of claim 1, wherein said water soluble, undissolved silica-based material is sol-gel derived.

7. The storage method of claim 1, wherein the sol-gel derived material is immersed in said liquid phase only after the sol-gel derived has been aged and/or dried such that the weight of the sol-gel derived is ≤90% of the weight of sol wherefrom the material was derived.

8. The storage method of claim 1, wherein a desired property of the undissolved silica-based material is preserved during storage.

9. The storage method of claim 1, wherein said living micro-organism or a spore thereof is selected from the group consisting of bacteria, protozoa and fungi.

10. A package containing an implant or delivery device, said package comprising:

i.) an essentially closed housing enclosing an implant or delivery device immersed within a liquid phase comprising water, wherein a) said implant or delivery device comprises a water-soluble, undissolved silica-based material prepared from an alkoxide and of which at least 50%, calculated as silicon dioxide ($SiO_2$) of dry matter, comprises $SiO_2$ and/or hydrolysed $SiO_2$, with a functional agent incorporated therein;

b) said liquid phase is saturated with a water-soluble silica-based material, which is the same or different than said water-soluble, undissolved silica-based material, such that said water-soluble, undissolved silica-based material does not at all or does not essentially dissolve into said liquid phase during storage, or an amount of said water-soluble, undissolved silica-based material is dissolved into said liquid phase, thereby saturating the liquid phase, with the proviso that the dissolved amount of said water-soluble silica-based material is less than 20% of an initial amount of said water-soluble, undissolved silica-based material;

and wherein the functional agent is a biologically active agent selected from the group consisting of viruses, a living micro-organism or a spore thereof, living animal cells, living plant cells and a nucleic acid.

11. The package of claim 10, wherein the liquid phase comprises more than 20 ppm of Si calculated as $SiO_2$.

12. The package of claim 10, wherein said micro-organism is selected from the group consisting of bacteria, protozoa and fungi.

13. The package of claim 10, wherein said functional agent is a nucleic acid.

14. The package of claim 10, wherein said delivery device is adapted for oral, buccal, rectal, parenteral, pulmonary, nasal, ocular, intrauterine, vaginal, urethral, topical or transdermal drug delivery.

15. The package of claim 10, wherein said implant is a member of the group consisting of a medical device, a tissue engineering scaffold, a prosthesis and an injectable device.

\* \* \* \* \*

UNITED STATES PATENT AND TRADEMARK OFFICE
CERTIFICATE OF CORRECTION

PATENT NO. : 9,226,893 B2  
APPLICATION NO. : 12/301195  
DATED : January 5, 2016  
INVENTOR(S) : Jokinen et al.

Page 1 of 1

It is certified that error appears in the above-identified patent and that said Letters Patent is hereby corrected as shown below:

IN THE CLAIMS:

Column 15, Lines 25, 26 and 27

Claim 7, line 3, change "sol-gel derived" to -- sol-gel derived material --;
  line 4, change "sol-gel derived" to -- sol-gel derived material --; and
  line 5, change "the material" to -- the sol-gel derived material --.

Signed and Sealed this
Thirty-first Day of May, 2016

Michelle K. Lee
*Director of the United States Patent and Trademark Office*